(12) United States Patent
Fernandez

(10) Patent No.: US 10,579,742 B1
(45) Date of Patent: Mar. 3, 2020

(54) BIOMETRIC SIGNAL ANALYSIS FOR COMMUNICATION ENHANCEMENT AND TRANSFORMATION

(71) Applicant: UIPCO, LLC, San Antonio, TX (US)

(72) Inventor: Amanda S. Fernandez, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 0 days.

(21) Appl. No.: 15/671,641

(22) Filed: Aug. 8, 2017

Related U.S. Application Data

(60) Provisional application No. 62/381,170, filed on Aug. 30, 2016.

(51) Int. Cl.
*G06F 17/28* (2006.01)
*G06F 17/22* (2006.01)
(Continued)

(52) U.S. Cl.
CPC ........ *G06F 17/2881* (2013.01); *A61B 5/0002* (2013.01); *A61B 5/165* (2013.01);
(Continued)

(58) Field of Classification Search
CPC .. G06F 17/28; G06F 17/2809; G06F 17/2818; G06F 17/2827; G06F 17/2836;
(Continued)

(56) References Cited

U.S. PATENT DOCUMENTS 7,487,093 B2 * 2/2009 Mutsuno ............... G10L 13/033
704/258
8,296,124 B1 * 10/2012 Holsztynska ....... G06F 17/2854
704/2
(Continued)

OTHER PUBLICATIONS

An, "How accurate is Google Translate, really?" Digital Trends, http://www.digitaltrends.com/web/how-accurate-is-google-translate/, Dated Apr. 27, 2013, pp. 1-11.
(Continued)

*Primary Examiner* — Lamont M Spooner
(74) *Attorney, Agent, or Firm* — Fletcher Yoder P.C.

(57) ABSTRACT

Techniques are described for data transformation performed based on a current emotional state of the user who provided input data, the emotional state determined based on biometric data for the user. Sensor(s) may generate biometric data that indicates physiological characteristic(s) of the user, and an emotional state of the user is determined based on the biometric data. Different dictionaries and/or dictionary entries may be used in translation, depending on the emotional state of the sender when the data was input. In some implementations, the emotional state of the sending user may be used to infer or otherwise determine that a translation was incorrect. The input data may be transformed to include information indicating the current emotional state of the sending user when they provided the input data. For example, the output text may be presented in a user interface with an icon and/or other indication of the sender's emotional state.

19 Claims, 7 Drawing Sheets

(51) Int. Cl.
*G10L 25/63* (2013.01)
*G10L 15/16* (2006.01)
*A61B 5/00* (2006.01)
*A61B 5/16* (2006.01)
*H04L 12/58* (2006.01)

(52) U.S. Cl.
CPC .......... *G06F 17/2276* (2013.01); *G10L 15/16* (2013.01); *G10L 25/63* (2013.01); *H04L 51/046* (2013.01)

(58) Field of Classification Search
CPC ............. G06F 17/2845; G06F 17/2854; G06F 17/2863; G06F 17/2872; G06F 17/289; G06F 17/2881
USPC ........................................................ 704/2–8
See application file for complete search history.

(56) References Cited

U.S. PATENT DOCUMENTS

| | | | | |
|---|---|---|---|---|
| 8,682,640 | B2* | 3/2014 | Jaiswal | G10L 15/005 704/2 |
| 9,262,688 | B1* | 2/2016 | Zadeh | G06N 7/02 |
| 9,836,128 | B2* | 12/2017 | Eun | G06F 3/017 |
| 2001/0029455 | A1* | 10/2001 | Chin | G06F 17/273 704/277 |
| 2007/0208569 | A1* | 9/2007 | Subramanian | G10L 19/0018 704/270 |
| 2011/0125486 | A1* | 5/2011 | Jaiswal | G06F 17/289 704/3 |
| 2011/0314451 | A1* | 12/2011 | Baumann | G06F 9/454 717/125 |
| 2012/0166180 | A1* | 6/2012 | Au | G06F 17/274 704/9 |
| 2013/0152000 | A1* | 6/2013 | Liu | G06F 9/44 715/765 |
| 2013/0185049 | A1* | 7/2013 | Zhao | G06F 17/2827 704/2 |
| 2013/0215275 | A1* | 8/2013 | Berini | G06F 21/32 348/150 |
| 2014/0244237 | A1* | 8/2014 | Srinivasan | G06F 17/289 704/2 |
| 2014/0258979 | A1* | 9/2014 | Zhang | G06F 8/70 717/120 |
| 2015/0142704 | A1* | 5/2015 | London | G06F 16/90332 706/11 |
| 2015/0338917 | A1* | 11/2015 | Steiner | H04L 9/3231 345/156 |
| 2016/0140966 | A1* | 5/2016 | Mines | G10L 15/26 704/235 |
| 2016/0170975 | A1* | 6/2016 | Jephcott | A61B 5/7465 704/3 |
| 2016/0343368 | A1* | 11/2016 | Yassa | G06F 17/289 |
| 2016/0350204 | A1* | 12/2016 | Conlon | G06F 11/3612 |
| 2017/0212890 | A1* | 7/2017 | Akbik | G06F 17/2785 |
| 2017/0251985 | A1* | 9/2017 | Howard | A61B 5/7282 |
| 2018/0046916 | A1* | 2/2018 | Dally | G06N 3/063 |
| 2018/0060757 | A1* | 3/2018 | Li | G06K 9/6256 |
| 2019/0028689 | A1* | 1/2019 | Aaron | G06K 9/00362 |

OTHER PUBLICATIONS

Balk et al, "Assessing the Accuracy of Google Translate to Allow Data Extraction From Trials Published in Non-English Languages [Internet]", NIH, NCBI, http://www.ncbi.nlm.nih.gov/books/NBK121306/, Dated Jan. 2013, pp. 1-42.

Green et al, "The efficacy of human post-editing for language translation." Proceedings of the SIGCHI conference on human factors in computing systems. ACM, Dated Apr. 27-May 2, 2013, pp. 1-10.

* cited by examiner

US 10,579,742 B1

BIOMETRIC SIGNAL ANALYSIS FOR COMMUNICATION ENHANCEMENT AND TRANSFORMATION

CROSS-REFERENCE TO RELATED APPLICATION

The present disclosure is related to, and claims priority to, U.S. Provisional Patent Application Ser. No. 62/381,170, titled "Biometric Signal Analysis for Data Transformation," which was filed on Aug. 30, 2016, the entirety of which is incorporated by reference into the present disclosure.

BACKGROUND

Translating from one natural language to another is a challenging problem to solve using computer software, given the complexity that is inherent in natural languages that have evolved over millennia through use in different societies. In general, natural language processing (NLP) techniques have been developed to analyze spoken or written input and translate the input to generate output in a different designated natural language. Existing, traditional translation solutions may translate each word or phrase individually, and may therefore introduce translation errors through lack of contextual awareness. Traditional translation solutions may exhibit translation errors in instances where words have a similar spelling and/or sound (e.g., "be" vs. "bee", "dye" vs. "die", etc.). Also, traditional translation solutions may also generate translated sentences in an order that is different than the order that would normally be used in the output language. Further, traditional transcription solutions that are intended to transcribe speech to text may also exhibit errors due to lack of contextual awareness, similar sounding words (e.g., homophones, homonyms) in the input, and/or other causes.

SUMMARY

Implementations of the present disclosure are generally directed to enhancing and/or transforming data that is transmitted in communications. More specifically, implementations are directed to enhancing, translating, and/or transforming data that is communicated between users, based at least partly on an emotional state of a sending user who provides the data to be communicated to a receiving user, the emotional state determined based at least partly on biometric data describing a current physiological state of the sending user.

In general, innovative aspects of the subject matter described in this specification can be embodied in methods that include actions of: receiving input data that is provided, by a first user, for communication to a second user; determining a state of the first user during a time period when the input data is provided, the state determined based on biometric data that is generated by at least one sensor device measuring at least one physiological characteristic of the first user during the time period; transforming the input data to generate output data, the transforming based at least partly on the state; and communicating the output data to be presented to the second user through a computing device.

Implementations can optionally include one or more of the following features: transforming the input data includes translating the input data from a first natural language to generate the output data in a second natural language; the translating employs at least one dictionary that provides a mapping from at least a portion of the input data to at least a portion of the output data, the mapping corresponding to the state; the translating includes performing a first translation of at least a portion of the input data from the first natural language to generate at least a portion of the output data in the second natural language, determining, based on the state, that the first translation is incorrect, and performing a second translation of at least the portion of the input data from the first natural language to generate at least the portion of the output data in the second natural language; communicating the output data causes an indicator to be presented to the second user, the indicator corresponding to the state of the first user; the output data is generated to include the indicator to be presented to the second user; the output data is generated to include metadata that corresponds to at least one of the indicator or the state of the first user; the indicator includes one or more of an icon, a color, an image, a textual descriptor, or an audio signal; the biometric data indicates one or more of heart rate, pulse, perspiration level, blood pressure, galvanic skin response, pupil dilation, or neural oscillation activity; the input data includes audio data of speech of the first user; the output data includes a text transcription of at least a portion of the audio data; and/or transforming the input data to generate the output data employs a convolutional neural network including at least one layer that performs an analysis based on the state of the first user.

Other implementations of any of the above aspects include corresponding systems, apparatus, and computer programs that are configured to perform the actions of the methods, encoded on computer storage devices. The present disclosure also provides a computer-readable storage medium coupled to one or more processors and having instructions stored thereon which, when executed by the one or more processors, cause the one or more processors to perform operations in accordance with implementations of the methods provided herein. The present disclosure further provides a system for implementing the methods provided herein. The system includes one or more processors, and a computer-readable storage medium coupled to the one or more processors having instructions stored thereon which, when executed by the one or more processors, cause the one or more processors to perform operations in accordance with implementations of the methods provided herein.

Implementations of the present disclosure provide one or more of the following technical advantages and improvements over traditional systems. Traditional translation methods may focus on the words that are communicated and may fail to account for the intent and/or context underlying the words. Accordingly, using traditional methods the state, intent, tone, and/or other context may be lost in translation. Implementations improve on traditional methods through the use of biometric data to determine a current emotional state of the person who spoke or wrote the input. The emotional state is employed during the translation process, as described below, to preserve the tone, intent, and/or context of the person when they spoke or wrote the input data. Accordingly, through the use of biometrically determined emotional state information for a sending user, implementations provide for translation of input data that may be more accurate than translation using traditional techniques. Accordingly, implementations make more efficient use of computing resources such as processing capacity, memory, storage, and/or network bandwidth compared to traditional translation systems that may consume computing resources through multiple failed attempts at translation.

Moreover, traditional methods for communicating speech and/or text data between users may not convey tone or intent. For example, using a traditional messaging system a sending user may provide input speech data which is transcribed to text for presentation in a receiving user's messaging client application. As another example, users may be exchanging text messages using a messaging and/or chat service. In either scenario, the sending user's tone, intent, and/or other context may be lost in the transcription and/or communication process, such that the receiver has no way of knowing when the sender is being earnest and/or literal in their communication, compared to instances when the sender may be sarcastic, ironic, or otherwise attempting to convey some non-literal nuance with their input data. Implementations also employ emotional state information to provide additional context in such situations, by presenting output data to the receiving user along with an indication of the sending user's emotional state when they input the data to be sent. Accordingly, implementations provide an improvement over traditional techniques for natural language translation, text-based communication, and text-based communication with a speech input interface, by using a biometrically determined emotional state of the sending user to preserve the intent, tone, nuance, and/or other context that may otherwise be lost using traditional techniques. Accordingly, implementations make more efficient use of computing resources such as network bandwidth compared to traditional messaging systems, in which users may be required to send one or more follow-up messages to clarify an initial message that is unclear in its emotional context and/or intent.

It is appreciated that aspects and features in accordance with the present disclosure can include any combination of the aspects and features described herein. That is, aspects and features in accordance with the present disclosure are not limited to the combinations of aspects and features specifically described herein, but also include any combination of the aspects and features provided.

The details of one or more implementations of the present disclosure are set forth in the accompanying drawings and the description below. Other features and advantages of the present disclosure will be apparent from the description and drawings, and from the claims.

DETAILED DESCRIPTION

Figure 1:
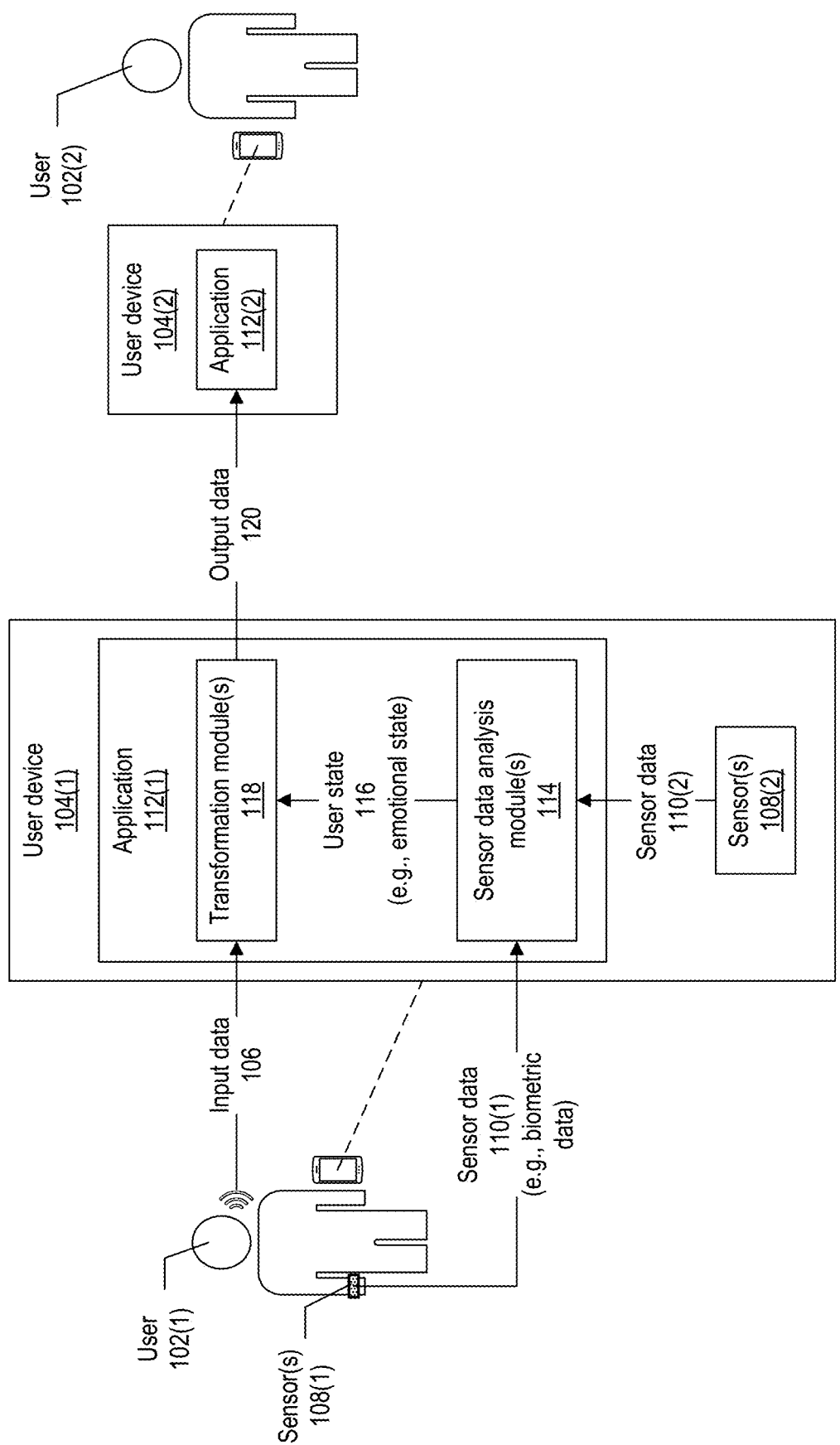
FIG. 1 depicts an example system for data transformation based on biometric sensor data analysis, according to implementations of the present disclosure.

Implementations of the present disclosure are directed to data transformation such as a natural language (NL) translation that is performed at least partly based on a current emotional state of the user who provided the input data, the emotional state determined based on biometric data for the user. One or more sensors in proximity to a user may generate biometric data that indicates one or more physiological characteristics of the user, such as the user's heart rate, pulse, blood pressure, perspiration level, brain wave activity, pupil dilation, galvanic skin response, and so forth. An emotional state of the user may be determined based on the biometric data. For example, biometric data may be used to determine whether the user is happy, sad, angry, calm, agitated, nervous, stressed, relaxed, and/or in some other state. The user may provide input data such as audio input (e.g., speech) and/or text input to be communicated to another user, e.g., during a text messaging (e.g., chat) session or other scenario. The determined emotional state of the sending user may be used to transform the input data to generate output data that is communicated to the receiving user.

In some implementations, the input data may be translated from one NL to another NL, and the current emotional state of the sending user may be used to determine particular dictionary entries to use during the translation. For example, a particular word in a first language may translate to different words in a second language depending on the emotional context in which the input word is uttered. Implementations may access different dictionaries and/or different dictionary entries to use in the translation, depending on the emotional state of the sender when the word was input. A dictionary entry may provide a mapping between a word (or phrase) in the input language and at least one output word (or phrase) in the output language.

In some implementations, the emotional state of the sending user may be used to infer or otherwise determine that a translation was incorrect, such that another attempt at translation may be needed. For example, a (e.g., bilingual) sending user may see that a word X in an input language was translated to a word Q in an output language. If the translation is not correct, or at least not the output that is ideal or desired by the sending user, the user's emotional state may become angry, frustrated, agitated, and so forth. On detecting that the user is in such a state or has entered such a state during a time when the translated output has been presented to the user, implementations may perform another attempt at translating the word. Any appropriate number of iterations may be performed until the user's emotional state indicates a likelihood that they are satisfied with the output of the translation.

In some implementations, the input data may be transformed to include information indicating the current emotional state of the sending user when they provided the input data. For example, the sending user may be using a speech-to-text feature of a chat program or messaging client while communicating with the receiving user. Implementations may transcribe the user's speech input to generate output text, which is then communicated for presentation to the receiving user. The emotional state of the sending user may be monitored, and an indication of the sending user's emotional state may be sent with the transcription. The output text may be presented, along with an indication of the sender's emotional state, to provide the receiving user with some context regarding the sender's emotional state. For example, the output text may be presented in a user interface (UI) with an icon, image, color, and/or other indication of the sender's emotional state when they entered the input data.

Traditional translation methods may focus on the words that are communicated and may fail to account for the intent and/or context underlying the words. A traditional algorithm may receive input from a user and individually translate the words or phrases of the input using a dictionary. The dictionaries that are traditionally used in NL translation processes may be more or less comprehensive. Although much research has been performed to configure dictionaries for translating words and/or phrases from one NL to another, even the most comprehensive dictionary may fail to account for the emotional state, intent, tone, and/or other current context of the person who spoke or wrote the input data to be translated. Accordingly, using traditional methods the state, intent, tone, and/or other context may be lost in translation. Implementations improve on traditional methods through the use of biometric data to determine a current emotional state of the person who spoke or wrote the input. The emotional state is employed during the translation process, as described below, to preserve the tone, intent, and/or context of the person when they spoke or wrote the input data.

Moreover, traditional methods for communicating speech and/or text data between users may not convey tone or intent. For example, using a traditional messaging system a sending user may provide input speech data which is transcribed to text for presentation in a receiving user's messaging client application. As another example, users may be exchanging text messages using a messaging and/or chat service. In either scenario, the sending user's tone, intent, and/or other context may be lost in the transcription and/or communication process, such that the receiver has no way of knowing when the sender is being earnest and/or literal in their communication, compared to instances when the sender may be sarcastic, ironic, or otherwise attempting to convey some non-literal nuance with their input data. Implementations also employ emotional state information to provide additional context in such situations, by presenting output data to the receiving user along with an indication of the sending user's emotional state when they input the data to be sent. Accordingly, implementations provide an improvement over traditional techniques for NL translation, text-based communication, and text-based communication with a speech input interface, by using a biometrically determined emotional state of the sending user to preserve the intent, tone, nuance, and/or other context that may otherwise be lost using traditional techniques.

FIG. 1 depicts an example system for data transformation based on biometric sensor data analysis, according to implementations of the present disclosure. As shown in the example, two users 102(1) and 102(2) may respectively use user devices 104(1) and 104(2) to communicate with one another. In some instances, the communications may be exchanged during a communication session in which any number of communications (e.g., messages) are sent and received between the users 102. A session may include any suitable number of communications over a period of time, and there may be a delay between the communications during a session. In some instances, communications may overlap such that a user 102(1) is reading or hearing a communication from the user 102(2) while the user 102(1) is speaking or composing another communication to the user 102(2). In some instances, the communications may be audio communications, e.g., during a telephone conversation, voice chat session, video chat session, an exchange of voice mail messages, and so forth. In some instances, the communications may be textual communications, e.g., during a chat session using a chat or messaging client, an exchange of Short Message Service (SMS) and/or Multimedia Messaging Service (MMS) messages, and so forth. Implementations also support other types of communications.

The user devices 104(1) and 104(2) may include any suitable type of computing device, including portable computing device(s) (e.g., smartphone, tablet computer, wearable computer, etc.) and less portable computing device(s) (e.g., laptop computer, desktop computer, etc.). The user device 104(1) and/or user device 104(2) may execute an application 112 that facilitates communications between the users 102. For example, the application 112 may be a chat client for entering, sending, receiving, and presenting communications that include text data, audio data, video data, and/or other types of data.

The user 102(1) (e.g., a sending user) may provide input data 106, such as text input and/or audio input (e.g., speech). The input data 106 may be received by the application 112(1) executing on the user device 104(1). The application 112(1) may also receive sensor data 110 generated by various sensor(s) 108 in proximity to the user 102(1). The sensor(s) 108 may also be described as sensor device(s). The sensor(s) 108 proximal to the user 102(1) may include sensor(s) that are in physical contact with the user 102(1), such as sensor(s) that are worn by the user 102(1) and/or implanted into the user's body. The proximal sensor(s) 108 may also include sensor(s) that are situated externally to the user 102(1) but in proximity to the user 102(1), e.g., near enough to collect image data, video data, audio data, thermal data, chemical data (e.g., odor information), and/or other data regarding the user 102(1).

In some implementations, the sensor data 110 may include sensor data 110(1) that is generated by sensor(s) 108(1) that are external to the user device 104(1) and in proximity to the user 102(1). Such sensor(s) 108(1) may be included in a wearable device such as a fitness tracking device, and the sensor(s) 108(1) may communicate the sensor data 110(1) to the user device 104(1) over one or more (e.g., wireless) networks using BlueTooth™, BlueTooth Low Energy™, or any other suitable network communication protocol. The sensor data 110 may include sensor data 110(2) that is generated by sensor(s) 108(2) that are incorporated into the user device 104(1) and in proximity to the user 102(1).

In some implementations, the sensor data 110 (e.g., sensor data 110(1) and/or 110(2)) includes biometric data that describes a physiological state and/or characteristic of the user 102(1). For example, the sensor data 110 may indicate a current value (e.g., when the user composes and/or provides the data to be communicated) of one or more of the following characteristics of the user 102(1): heart rate, pulse, blood pressure, perspiration level, blood sugar level, body temperature, respiration rate, pupil dilation, galvanic skin response (e.g., electrodermal activity), and/or brain wave activity (e.g., neuro-electrical activity). In some implementations, the biometric data may include data describing voluntary and/or involuntary movements of the user 102(1) such as jitters, tremors, eye movements, nervous movements (e.g., tapping figures), and so forth.

The user device 104(1) may execute one or more sensor data analysis modules 114. The sensor data analysis module(s) 114 may execute as sub-module(s) of the application 112(1) (e.g., as shown in FIG. 1). In some implementations, the sensor data analysis module(s) 114 may execute separately, e.g., as separate processes, relative to the application 112(1). The sensor data analysis module(s) 114 may receive the sensor data 110, e.g., sensor data 110(1) and/or sensor data 110(2), and analyze the sensor data 110 to determine a current user state 116 of the user 102(1) based on the sensor data 110. In some implementations, the user state 116 may be an emotional state of the user 102(1), indicating whether the user 102(1) is happy, sad, angry, calm, agitated, nervous, under stress, tired, sleepy, alert, and/or in some other state(s).

In some implementations, the biometric data indicating a physiological and/or health status of the user 102(1) may be collected and analyzed to determine the user's level of stress, anger, happiness, and/or other user state(s) 116. For example, an increase or other change in the user's heart rate, pulse, perspiration, galvanic skin response, brain wave activity, or other biometric data may indicate that the user 102(1) is angry, stressed, and/or otherwise agitated. In some implementations, images of at least a portion of the user's face (e.g., mouth, eyes, etc.) or posture (e.g., shoulders) may be analyzed using mood recognition analysis techniques to determine the emotional state (e.g., stress level) of the user 102(1).

In some implementations, at least a portion of the input data 106 may also be analyzed to determine the user state 116, in addition to or instead of analyzing the sensor data 110. For example, audio data of the voice of the user 102(1) may be analyzed using audio analysis techniques to detect mood and/or stress indicators in the user's voice and/or language usage. In some implementations, audio data of the voice of the user 102(1) may be transcribed using speech-to-text (STT) software, and the generated text may be analyzed using natural language processing (NLP), semantic analysis, keyword recognition, or other methods to detect indications of stress, anger, and/or other emotions in the user's language. In some implementations, text data communicated by the user 102(1) may be analyzed to determine a user state 116 of the user 102(1). For example, heightened emotions (e.g., anger) may lead to more misspellings or grammar errors, use of different vocabulary, use of a higher proportion of shorter words, different punctuation, and so forth. A change in the emotional state of the user 102(1) may also lead to an increase or decrease in typing speed, which may be detected and used to determine the user state 116.

The user device 104(1) may execute one or more transformation modules 118 that operate to transform the input data 106 to output data 120. The transformation module(s) 118 may execute as sub-module(s) of the application 112(1) (e.g., as shown in FIG. 1). In some implementations, the transformation module(s) 118 may execute separately, e.g., as separate processes, relative to the application 112(1). The transformation module(s) 118 may transform the input data 106 to generate the output data 120, and such transformation may be based at least partly on the current user state 116 of the user 102(1). In some implementations, transformation may include translating at least a portion of the input data 106 that is in a first NL to generate the output data 120 in a second NL. Such implementations are described further with reference to FIGS. 2 and 3. In some implementations, transformation may include incorporating an emotional indicator into the input data 106 and/or into a text transcription of the input data 106. Such implementations are described further with reference to FIGS. 4 and 5.

The generated output data 120 may be communicated over one or more networks to a user device 104(2) of a receiving user 102(2). The output data 120 may be presented in a UI of an application 112(2) executing on the user device 104(2). Although the example of FIG. 1 depicts, for the sake of clarity, a one-way communication between the user device 104(1) and the user device 104(2), implementations are not so limited. In some instances, the users 102(1) and 102(2) may communicate back-and-forth using the user devices 104 and the applications 112, e.g., during a text chat or voice chat session. Accordingly, the user device 104(2) and/or application 112(2) may include the various components depicted in FIG. 1 on the sending side, such as the sensor(s) 108, the sensor data analysis module(s) 114, and/or the transformation module(s) 118. The user 102(2) may respond to the user 102(1) by providing their own input data, which may be transformed to output data based on the user state 116 of the user 102(2). Such output data may be communicated to the user 102(1) and/or user device 104(1).

In some implementations, the transformation module(s) 118 may employ one or more machine learning (ML) techniques to generate the output data 120 based on the user state 116. Such ML techniques may include, as appropriate, supervised and/or unsupervised ML technique(s). In some implementations, the transformation module(s) 118 may employ convolutional neural network(s) (CNN(s)) to determine the output data 120. A CNN is a type of artificial neural network (ANN), a machine learning framework that may employ layers of feature extraction followed by a classifier of these features. In some implementations, the classifier is replaced with a Support Vector Machine (SVM) for improved classification in certain applications. In some implementations, the CNN includes layers for speech and/or text recognition, intent tracking based on the user state 116, language translation, and/or dictionary-based verification. In this way, implementations may be described as employing a deep learning algorithm that employs multiple layers of processing, in which each layer is itself a ML algorithm. In some implementations, the transformation module(s) 118 may employ some other type of ANN, such as an ANN that employs data sampling that is more regular (e.g., non-stochastic) than the sampling which may be used in a CNN.

In some implementations, these layers are followed by a Support Matrix Machine (SMM) classifier, which may be employed instead of a SVM classifier. A SMM classifier may perform analysis based on a matrix of dimensions (e.g., M by N matrix) instead of a SVM classifier which may perform analysis based on a vector (e.g., 1 by N vector). Using a SVM classifier, the process may learn from the analyzed data (e.g., input data and/or user state) sequentially, e.g., analyzing one dimension at a time. Using a SMM classifier, the process may learn (e.g., simultaneously) across multiple dimensions by analyzing the correlations between dimensions. For example, a SMM may be used to correlate the relationship(s) between spoken or written text and an understanding of the language intent as indicated by the user state, and such correlation(s) may be correlated with possible translations of the input data.

Implementations may employ a SMM instead of a SVM, given that a SVM may be limited in scope by processing each portion of data individually. A SMM may enable the process to develop a deeper understanding of the adjacent data relative to the analyzed data, and determine relationships and/or context between the various dimensions of data being analyzed. In some implementations, a reduced version of a SMM may be employed. Such a SMM may include the dimensions that have the largest effect on the result. For example, a customer may call a service representative to discuss an insurance claim, and the dimensions that are correlated in a SVM may include the customer data and their claim data. Use of a SMM in this instance accounts for additional correlations between the current call and the customer's previous call and/or claim history. Such correlation(s) may help to identify instances of fraud, such as fraudulent insurance claims.

In some implementations, a model of the user 102(1) may be developed over time, the model indicating the typical user state 116 (e.g., emotional state) of the user 102(1). The model may be developed and refined based on the sensor data 110 collected that describes the user's physiological characteristics. In some implementations, an initial baselining and/or calibration may be performed to determine an initial model for the user 102(1). Alternatively, the model may be created when the user 102(1) begins user the user device 104(1) and/or application 112(1), and the model may be developed over time as additional sensor data 110 is collected and analyzed regarding the user 102(1). In some implementations, a current user state 116 of the user 102(1) may be relative to the typical user state indicated by the model of the user 102(1), e.g., whether the user is more or less angry than typical, more or less happy than typical, and so forth.

Figure 2:
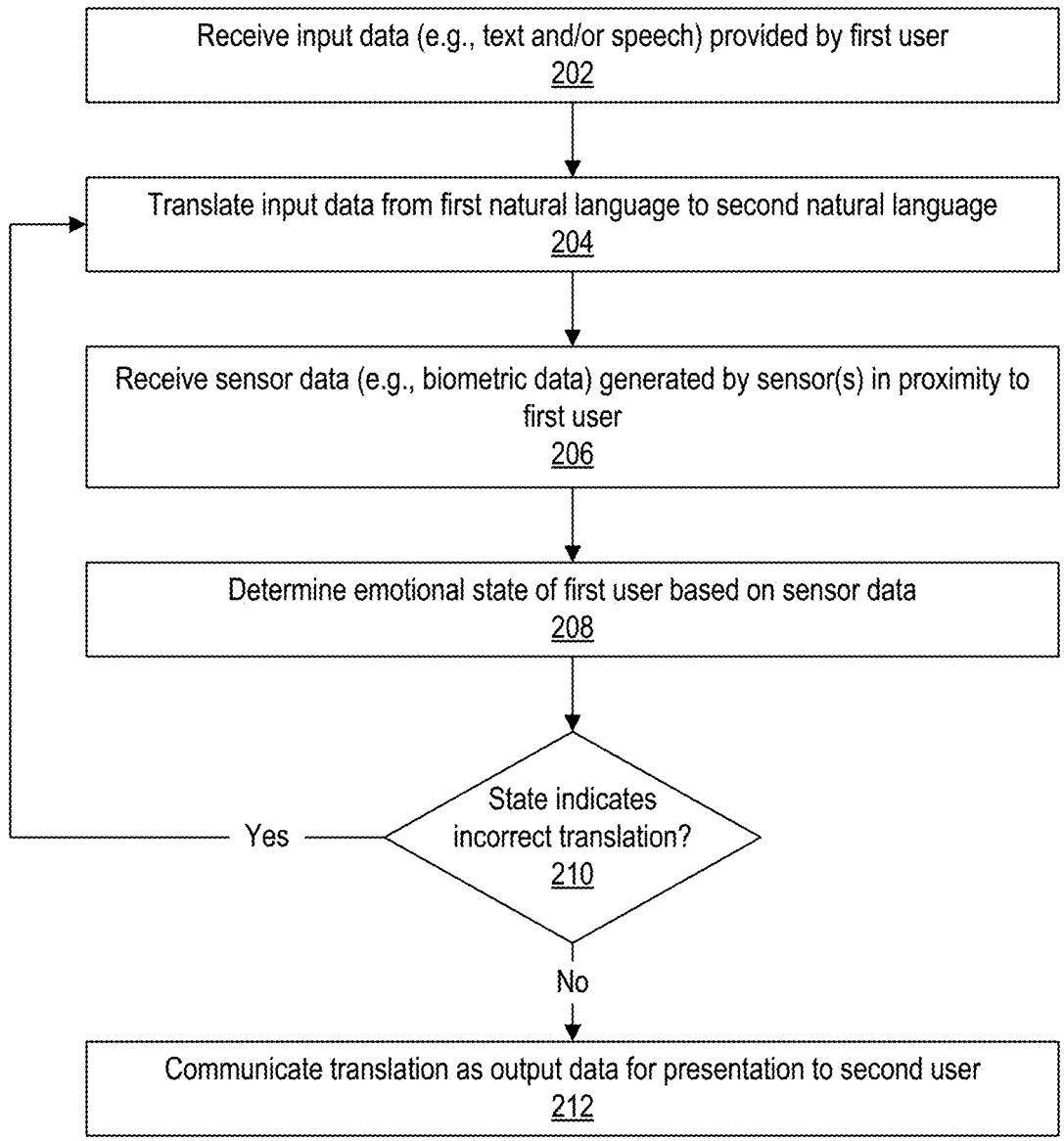
FIG. 2 depicts a flow diagram of an example process for detecting incorrect translation based on biometric sensor data analysis, according to implementations of the present disclosure.

FIG. 2 depicts a flow diagram of an example process for detecting incorrect translation and/or refining translation based on biometric sensor data analysis, according to implementations of the present disclosure. Operations of the process may be performed by one or more of the application 112, the sensor data analysis module(s) 114, the transformation module(s) 118, and/or other software module(s) executing on the user device(s) 104 or elsewhere.

The input data 106 may be received (202). As described above, input data 106 may include text data and/or audio data (e.g., speech input) provided by the user 102(1).

The input data 106 may be translated (204) from a first NL to a second NL. In some implementations, the second NL may be specified by the user 102(1). In some implementations, the second NL may be determined based on language preferences, location, and/or other characteristic(s) of the user 102(2) who is to receive the output data 120.

The sensor data 110 may be received (206). As described above, the sensor data 110 may include biometric data describing various physiological characteristic(s) of the user 102(1), and may be generated by one or more sensors 108 in proximity to the user 102(1).

The user state 116 of the user 102(1) may be determined (208) based on an analysis of the sensor data 110. As described above, the user state 116 may be an emotional state of the user 102(1). In some implementations, the sensor data 110 may be analyzed in real time as it is collected. Accordingly, the user state 116 may be a current user state of the user 102(1), current with respect to a time period during which the sensor data 110 is collected and analyzed. Moreover, the sensor data 110 may be collected and analyzed in real time with respect to the user providing the input data 106. The sensor data 110 may be collected and/or analyzed during a time period that includes, and/or is proximal in time to, a time when the user entered the input data 106 to be communicated. Accordingly, the user state 116 may be a current user state 116 of the user 102(1) when the user 102(1) is entering the input data 106, such as the state of the user when they entered a text message to be sent to another user, or spoke a phrase to be translated and/or transcribed and communicated to another user. Real time operation(s) may include the automatic performing of one or more operations without requiring human input and without any intentional delay with respect to a triggering event, taking into account the processing limitations of the computing system(s) performing the operations and the time needed to perform the operations. Accordingly, the analysis of the sensor data 110 may be performed in real time with respect to the collection of the sensor data 110, and the collection and/or analysis of the sensor data 110 may be performed in real time with respect to the user providing the input data 106 as speech and/or text input.

The output of the translation may be presented to the user 102(1). A determination may be made (210) whether the user's current state indicates that the translation may have been incorrect. For example, if the user's emotional state becomes angry, agitated, frustrated, and/or stressed when the translation is presented, an inference may be made that the translation is incorrect or in some way inappropriate. In such instances, the process may return to 204 and another attempt may be made to translate at least a portion of the input data 106 (e.g., using different dictionary entries).

If the user's emotional state stays the same when the translation is presented, or exhibits a positive change (e.g., the user becomes happy, calm, etc.), an inference may be made that the translation is correct or otherwise appropriate. The translated output data 120 may be communicated (212) for presentation to the user 102(2) on the user device 104(2).

In this way, implementations may employ the user state 116 of the user 102(1) as feedback to determine whether the translation was correct. Such feedback may also be employed to train, refine, or otherwise refine a ML-based classifier used to perform the translation of the input data 106 as described above. In some implementations, the user state 116 of the receiving user 102(2) may be monitored based on collected sensor data 110, and the receiving user's emotional state may be employed to refine the translation. For example, if the receiving user's emotional state is confused and/or agitated on receiving the translated output data 120, a determination may be made that the translation was incorrect and another attempt at translation may be performed on the sending user's user device 104(1).

Figure 3:
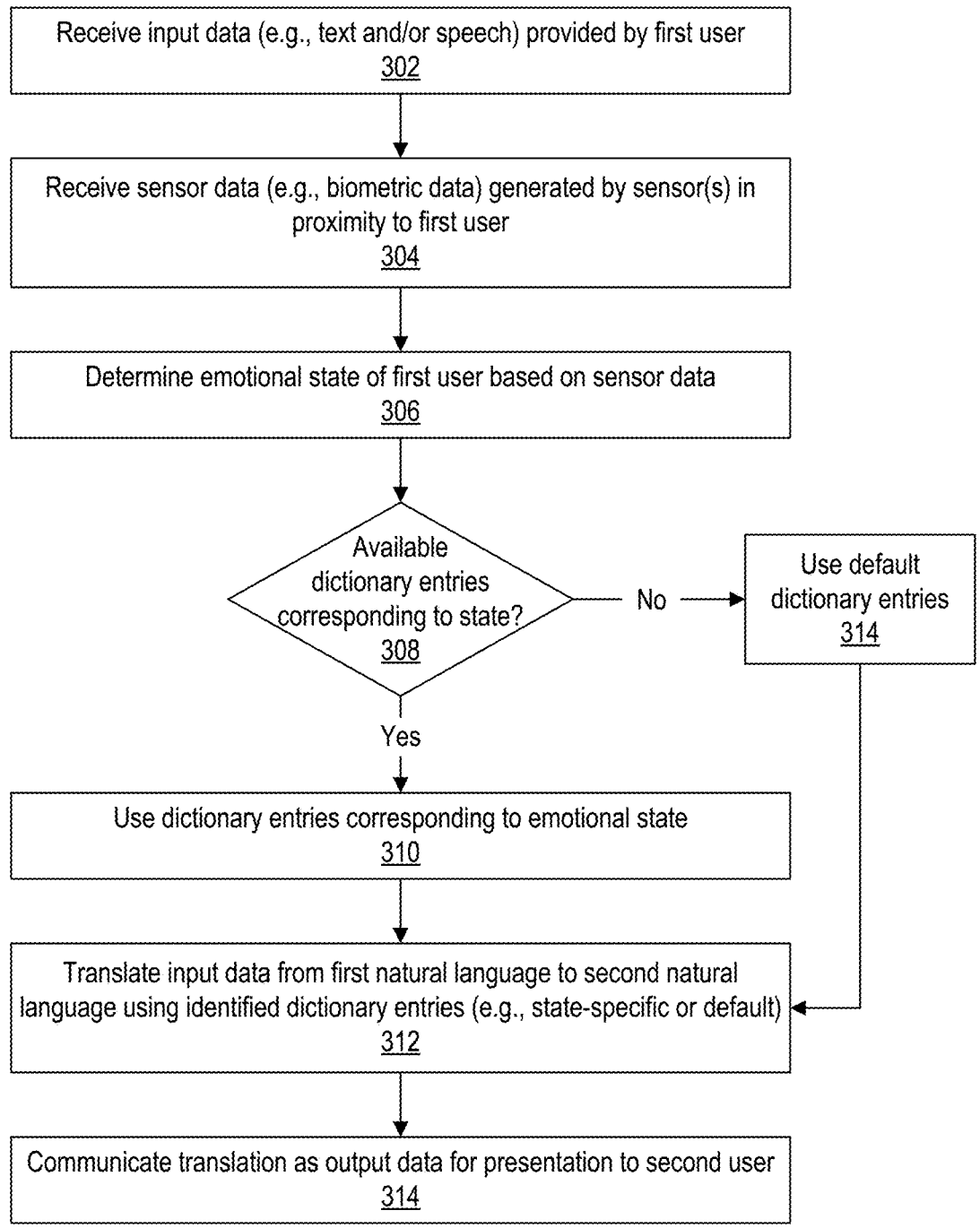
FIG. 3 depicts a flow diagram of an example process for translation based on biometric sensor data analysis, according to implementations of the present disclosure.

FIG. 3 depicts a flow diagram of an example process for translation based on biometric sensor data analysis, according to implementations of the present disclosure. Operations of the process may be performed by one or more of the application 112, the sensor data analysis module(s) 114, the transformation module(s) 118, and/or other software module(s) executing on the user device(s) 104 or elsewhere.

The input data 106 may be received (302). As described above, input data 106 may include text data and/or audio data (e.g., speech input) provided by the user 102(1).

The sensor data 110 may be received (304). As described above, the sensor data 110 may include biometric data describing various physiological characteristic(s) of the user 102(1), and may be generated by one or more sensors 108 in proximity to the user 102(1).

The user state 116 of the user 102(1) may be determined (306) based on an analysis of the sensor data 110. As described above, the user state 116 may be an emotional state of the user 102(1).

A determination may be made (308) whether there is an available dictionary that corresponds to the current state of the user 102(1), and/or whether there are one or more dictionary entries that are available and that correspond to the current state of the user 102(1). If so, the available dictionary and/or entries may be used (310) for translation. If not, a default dictionary and/or entries may be used (314).

The input data 106 may be translated (312) from a first NL to a second NL using the identified dictionary and/or dictionary entries. In some implementations, the second NL may be specified by the user 102(1). In some implementations, the second NL may be determined based on language preferences, location, and/or other characteristic(s) of the user 102(2) who is to receive the output data 120.

The translated output data 120 may be communicated (314) for presentation to the user 102(2) on the user device 104(2).

In some implementations, the process may have access to various dictionaries that translate from NL X to NL Y, and each dictionary may include entries that are suitable to translate based on a particular detected emotional state. In some implementations, the process may have access to a dictionary for translating from NL X to NL Y, and the dictionary may include a first set of entries suitable for translation during a first emotional state, and a second set of entries suitable for translation during a second emotional state. For example, a word or phrase in NL X may be appropriately translated to a particular word or phrase in NL Y if the speaker (or writer) is in a happy mood, and the same word or phrase in NL X may be appropriately translated to a different word or phrase in NL Y if the speaker (or write) is in an angry mood. In this way, implementations may employ the current emotional state of the sending user 102(1) to generate a more accurate translation of at least a portion of the user's input data 106 than would be otherwise generated using a default (e.g., emotion-agnostic) dictionary and/or dictionary entries.

In some implementations, a dictionary may be used which is specifically created and adapted for use in modifying the communications of the particular user (e.g., speaker or writer). In some implementations, the dictionary may be specific to a particular class or category of users that include the user, such as a demographic group (e.g., age range-based group) or location-based group (e.g., group of users in a particular region, country, city, etc.). The user-specific dictionary may provide a baseline for the particular user, and may be modified over time based on detected changes in the user's vocabulary, grammar, syntax, or other changes in written and/or spoken language usage. In some implementations, a dictionary may be used which is specific to both the particular user and the detected emotional state for the user. For example, a particular user may be associated with multiple dictionaries that correspond to different emotional states (e.g., angry, happy, sad, etc.). The dictionary that is used for translation and/or some other communication modification may be selected for the particular user and their current emotional state.

Figure 4:
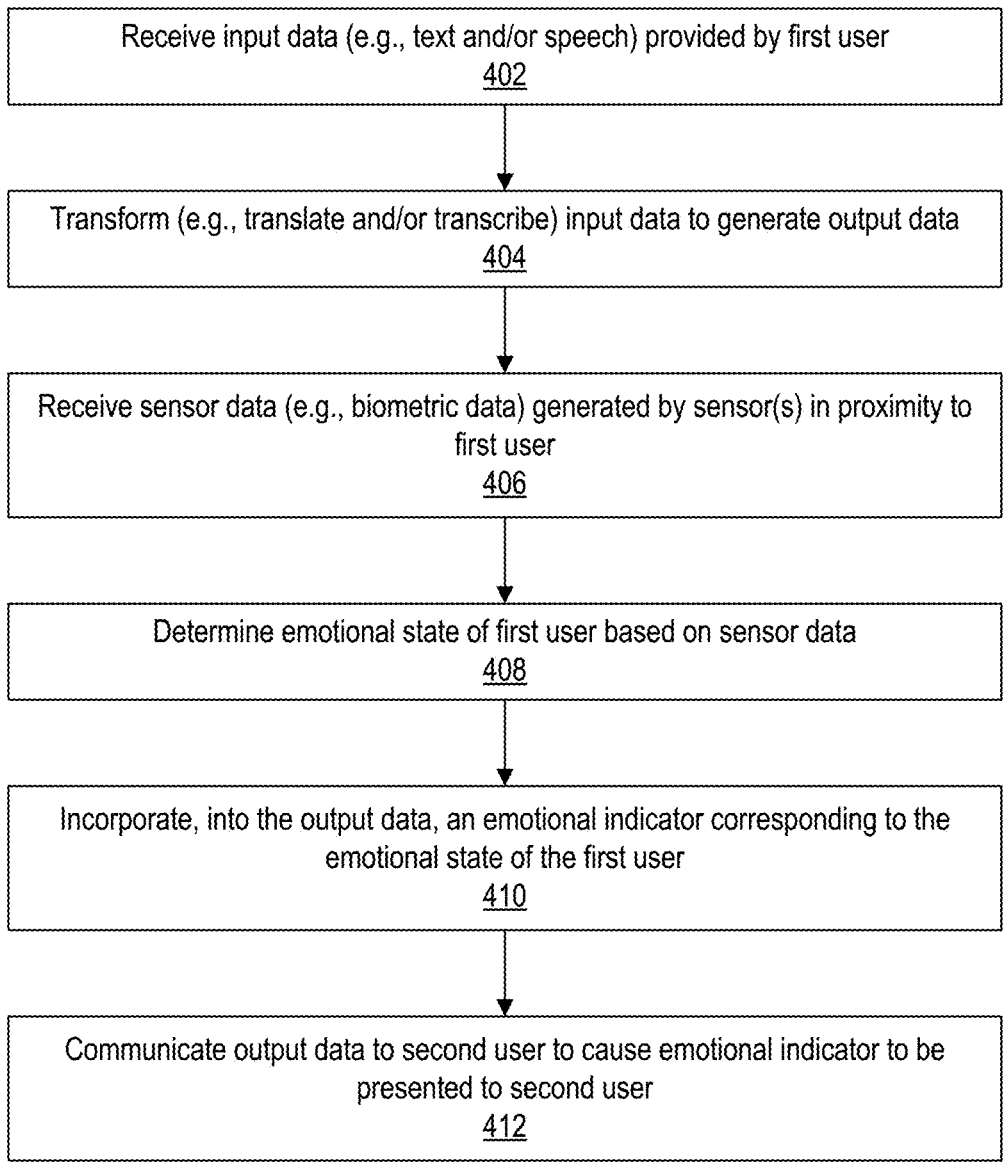
FIG. 4 depicts a flow diagram of an example process for providing a user state indicator for transformed data based on biometric sensor data analysis, according to implementations of the present disclosure.

FIG. 4 depicts a flow diagram of an example process for providing a user state indicator for transformed data based on biometric sensor data analysis, according to implementations of the present disclosure. Operations of the process may be performed by one or more of the application 112, the sensor data analysis module(s) 114, the transformation module(s) 118, and/or other software module(s) executing on the user device(s) 104 or elsewhere.

The input data 106 may be received (402). As described above, input data 106 may include text data and/or audio data (e.g., speech input) provided by the user 102(1).

In some instances, at least a portion of the input data 106 may be transformed (404). As described above, transformation may include translating the input data 106 from a first NL to a second NL. In some instances, transformation may include transcribing audio input data 106 to generate text data, e.g., through use of a speech recognition process and/or STT module.

The sensor data 110 may be received (406). As described above, the sensor data 110 may include biometric data describing various physiological characteristic(s) of the user 102(1), and may be generated by one or more sensors 108 in proximity to the user 102(1).

The user state 116 of the user 102(1) may be determined (408) based on an analysis of the sensor data 110. As described above, the user state 116 may be an emotional state of the user 102(1).

The input data 106 may be further transformed to incorporate (410), into the output data 120, an emotional indicator that corresponds to the user state 116 of the user 102(1).

The output data 120, including the emotional indicator, may be communicated (314) for presentation to the user 102(2) on the user device 104(2). The output data 120 may be presented along with the emotional indicator, to indicate to the user 102(2) the emotional state of the sending user 102(1) when the input data 106 was provided. In this way, implementations may send text data while conveying the emotional context and/or intent of the sending user.

Figure 5A:
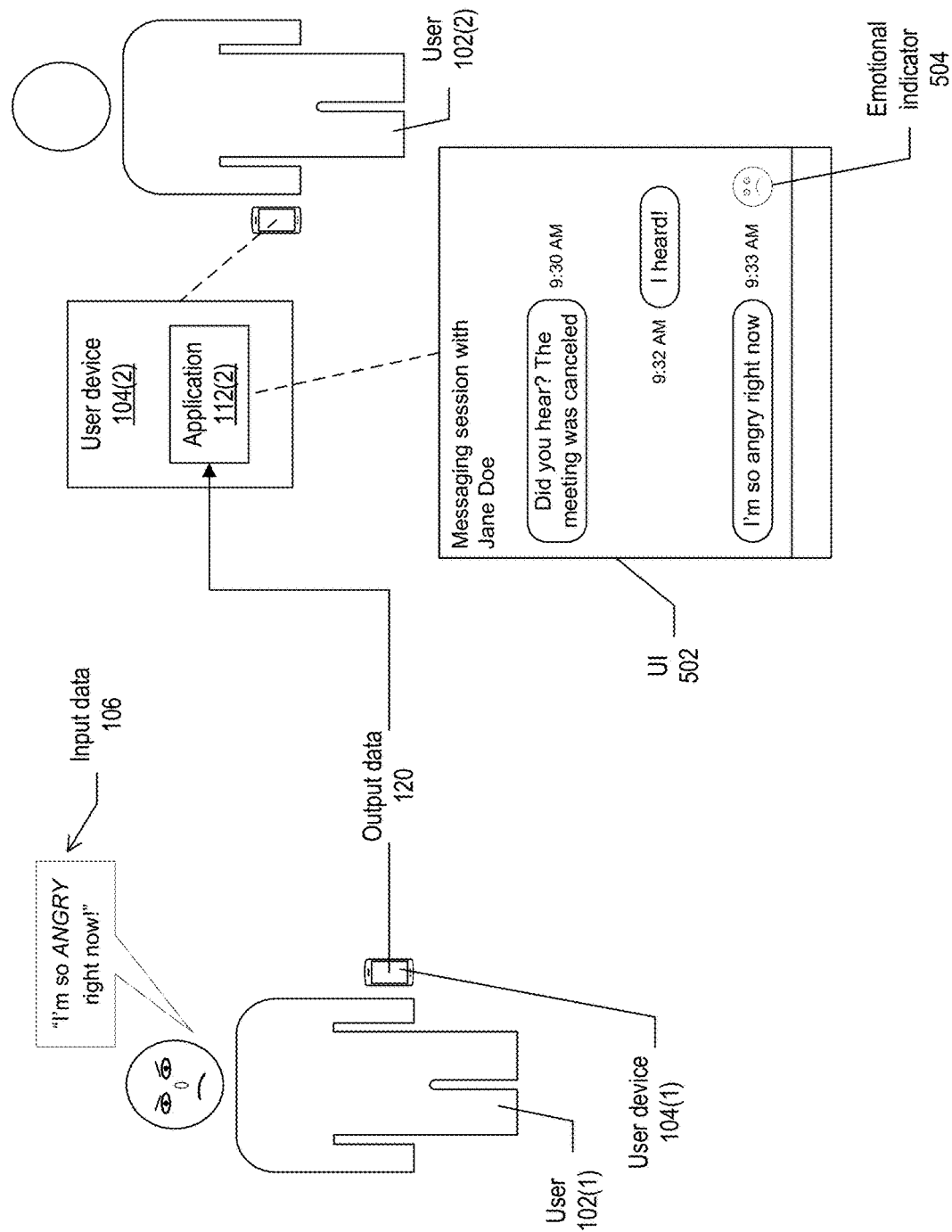
FIGS. 5A and 5B depict an example of a user state indicator presented in a user interface with transformed data, according to implementations of the present disclosure.
Figure 5B:
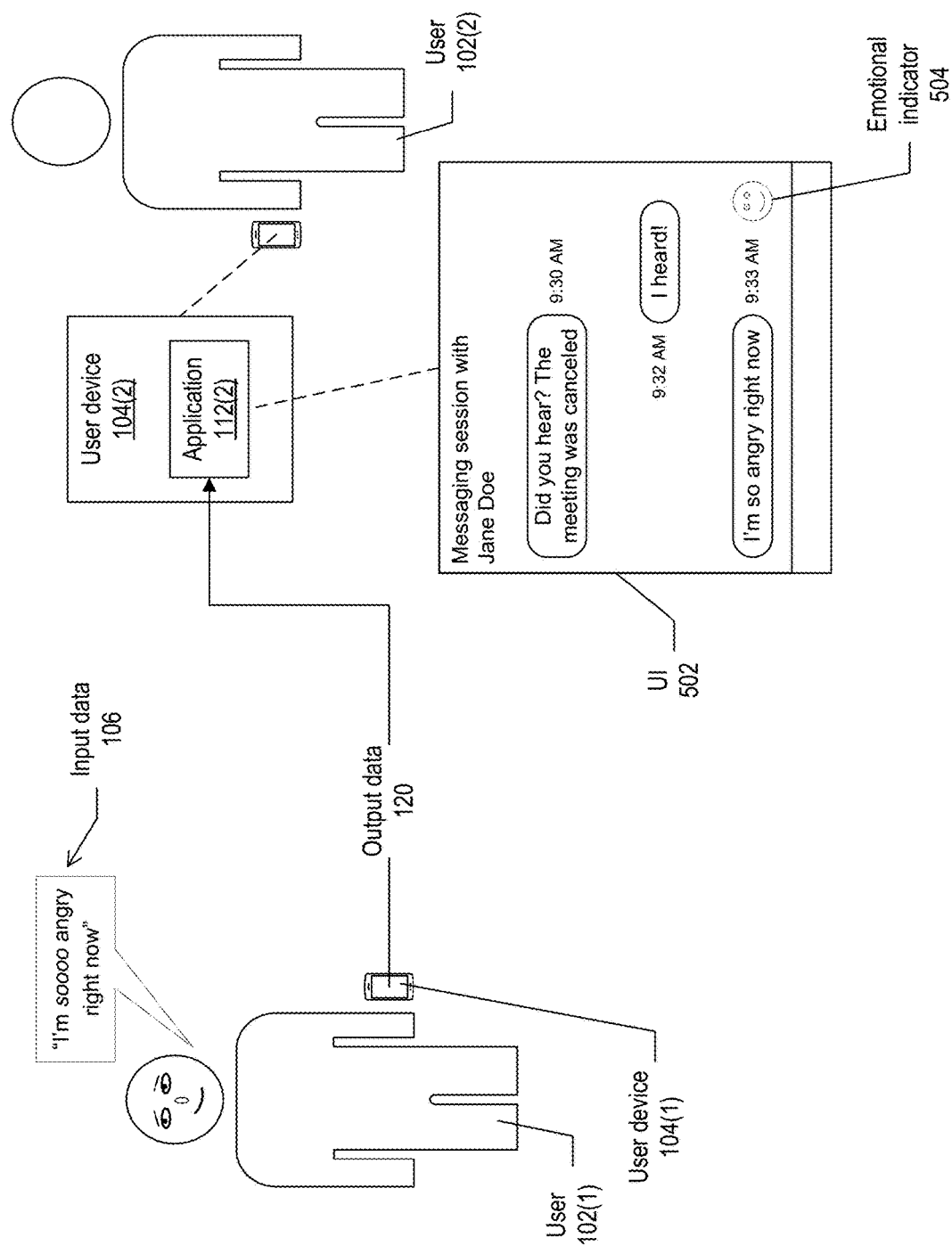

FIGS. 5A and 5B depict an example of a user state (e.g., emotional) indicator presented in a UI 502 with transformed data, according to implementations of the present disclosure. In some implementations, the UI 502 may be an interface of the application 112(2), such as a chat client, messaging client, and so forth.

In the example of FIG. 5A, the sending user 102(1) has spoken or typed the input data "I'm so angry right now," which is communicated as the output data 120 for presentation to the user 102(2) in the UI 502. In this example, the sensor data 110 is analyzed to determine that the user 102(1) is angry, so that the user statement "I'm so angry right now" is made when the user 102(1) is actually angry. The output data 120 "I'm so angry right now" is presented, through the UI 502, with an emotional indicator 504 indicating that the sending user's current state is anger.

In the example of FIG. 5B, the sending user 102(1) has spoken or typed the same input data "I'm so angry right now," which is communicated as the output data 120 for presentation to the user 102(2) in the UI 502. In this example, the sensor data 110 is analyzed to determine that the user 102(1) is currently happy, amused, or in some other way not angry. In this instance, the user statement "I'm so angry right now" may have been made by the user 102(1) ironically, sarcastically, or in some other way such that the literal meaning of the input data is not what the sending user was actually feeling at the time. The output data 120 "I'm so angry right now" is presented, through the UI 502, with an emotional indicator 504 indicating that the sending user's current state is happy, amused, or otherwise not angry.

Although FIGS. 5A and 5B depict the emotional indicator 504 as a face emoticon, implementations are not limited to this example. The emotional indicator 504 may include one or more of an emoticon, an icon, an emoji, a symbol, a graphic, a color, an image, a textual descriptor, and/or any other suitable visual indicator. In some implementations, the emotional indicator 504 may include audio data (e.g., an audio signal), such as one or more sounds or portions of music that indicate an emotional state. The emotional indicator 504 may include a visual indicator, an audio indicator, and/or any suitable combination of visual and/or audio indicator(s).

In some implementations, the emotional indicator 504 may be incorporated into the output data 120 and communicated to the user device 104(2) from the user device 104(1). In some implementations, the output data 120 may be transformed to include metadata that indicates an emotional state of the sending user 102(1). The metadata may be interpreted by the application 112(1) and/or UI 502 and used to determine an appropriate emotional indicator 504 to be presented in the UI 504 with the output data 120.

Figure 6:
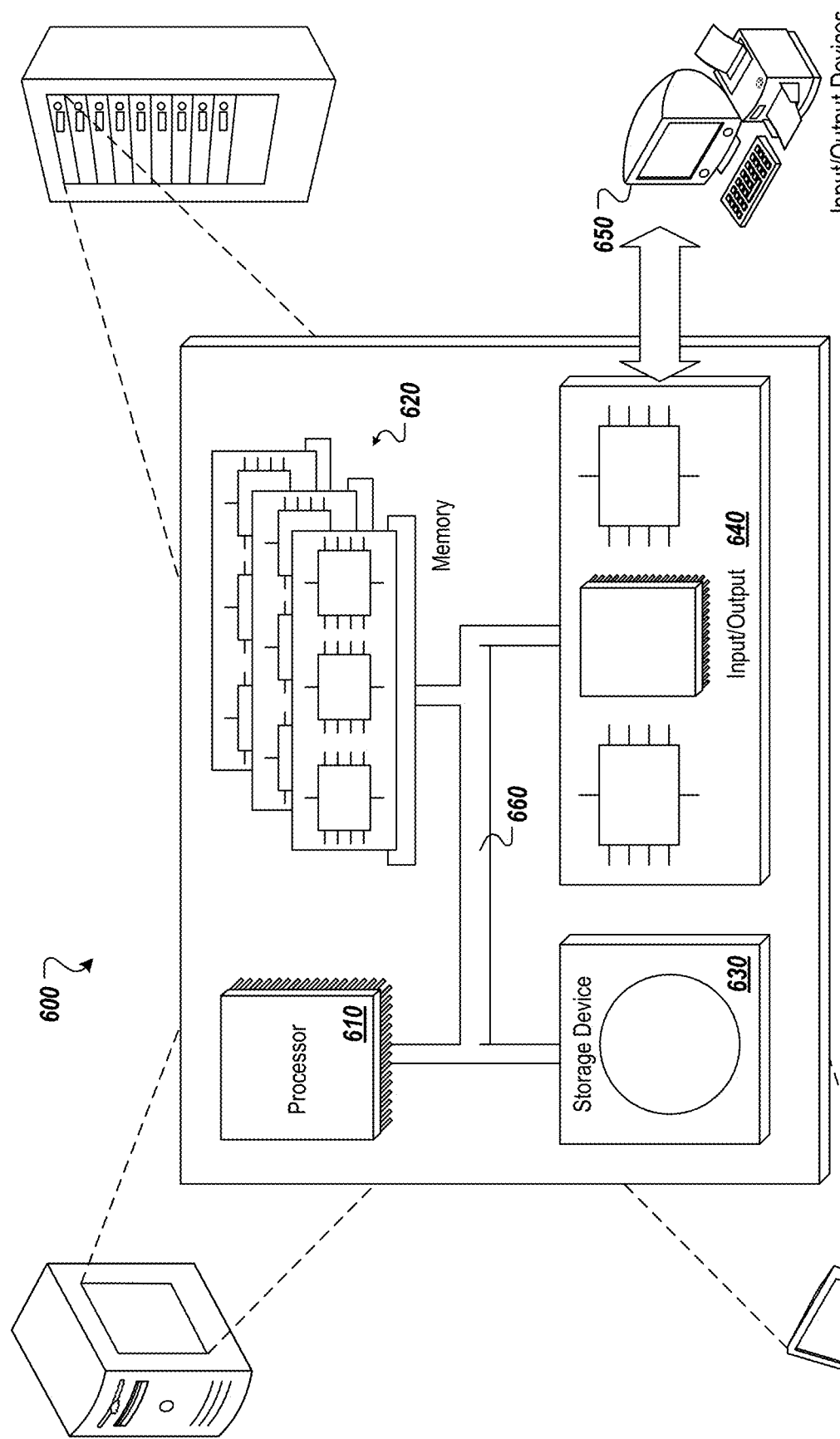
FIG. 6 depicts an example computing system, according to implementations of the present disclosure.

FIG. 6 depicts an example computing system, according to implementations of the present disclosure. The system 600 may be used for any of the operations described with respect to the various implementations discussed herein. For example, the system 600 may be included, at least in part, in one or more of the user device(s) 104 and/or other computing device(s) or system(s) described herein. The system 600 may include one or more processors 610, a memory 620, one or more storage devices 630, and one or more input/output (I/O) devices 650 controllable through one or more I/O interfaces 640. The various components 610, 620, 630, 640, or 650 may be interconnected through at least one system bus 660, which may enable the transfer of data between the various modules and components of the system 600.

The processor(s) 610 may be configured to process instructions for execution within the system 600. The processor(s) 610 may include single-threaded processor(s), multi-threaded processor(s), or both. The processor(s) 610 may be configured to process instructions stored in the memory 620 or on the storage device(s) 630. The processor(s) 610 may include hardware-based processor(s) each including one or more cores. The processor(s) 610 may include general purpose processor(s), special purpose processor(s), or both.

The memory 620 may store information within the system 600. In some implementations, the memory 620 includes one or more computer-readable media. The memory 620 may include any number of volatile memory units, any number of non-volatile memory units, or both volatile and non-volatile memory units. The memory 620 may include read-only memory, random access memory, or both. In some examples, the memory 620 may be employed as active or physical memory by one or more executing software modules.

The storage device(s) 630 may be configured to provide (e.g., persistent) mass storage for the system 600. In some implementations, the storage device(s) 630 may include one or more computer-readable media. For example, the storage device(s) 630 may include a floppy disk device, a hard disk device, an optical disk device, or a tape device. The storage device(s) 630 may include read-only memory, random access memory, or both. The storage device(s) 630 may include one or more of an internal hard drive, an external hard drive, or a removable drive.

One or both of the memory 620 or the storage device(s) 630 may include one or more computer-readable storage media (CRSM). The CRSM may include one or more of an electronic storage medium, a magnetic storage medium, an optical storage medium, a magneto-optical storage medium, a quantum storage medium, a mechanical computer storage medium, and so forth. The CRSM may provide storage of computer-readable instructions describing data structures, processes, applications, programs, other modules, or other data for the operation of the system 600. In some implementations, the CRSM may include a data store that provides storage of computer-readable instructions or other information in a non-transitory format. The CRSM may be incorporated into the system 600 or may be external with respect to the system 600. The CRSM may include read-only memory, random access memory, or both. One or more CRSM suitable for tangibly embodying computer program instructions and data may include any type of non-volatile memory, including but not limited to: semiconductor memory devices, such as EPROM, EEPROM, and flash memory devices; magnetic disks such as internal hard disks and removable disks; magneto-optical disks; and CD-ROM and DVD-ROM disks. In some examples, the processor(s) 610 and the memory 620 may be supplemented by, or incorporated into, one or more application-specific integrated circuits (ASICs).

The system 600 may include one or more I/O devices 650. The I/O device(s) 650 may include one or more input devices such as a keyboard, a mouse, a pen, a game controller, a touch input device, an audio input device (e.g., a microphone), a gestural input device, a haptic input device, an image or video capture device (e.g., a camera), or other devices. In some examples, the I/O device(s) 650 may also include one or more output devices such as a display, LED(s), an audio output device (e.g., a speaker), a printer, a haptic output device, and so forth. The I/O device(s) 650 may be physically incorporated in one or more computing devices of the system 600, or may be external with respect to one or more computing devices of the system 600.

The system 600 may include one or more I/O interfaces 640 to enable components or modules of the system 600 to control, interface with, or otherwise communicate with the I/O device(s) 650. The I/O interface(s) 640 may enable information to be transferred in or out of the system 600, or between components of the system 600, through serial communication, parallel communication, or other types of communication. For example, the I/O interface(s) 640 may comply with a version of the RS-232 standard for serial ports, or with a version of the IEEE 1284 standard for parallel ports. As another example, the I/O interface(s) 640 may be configured to provide a connection over Universal Serial Bus (USB) or Ethernet. In some examples, the I/O interface(s) 640 may be configured to provide a serial connection that is compliant with a version of the IEEE 1394 standard.

The I/O interface(s) 640 may also include one or more network interfaces that enable communications between computing devices in the system 600, or between the system 600 and other network-connected computing systems. The network interface(s) may include one or more network interface controllers (NICs) or other types of transceiver devices configured to send and receive communications over one or more networks using any network protocol.

Computing devices of the system 600 may communicate with one another, or with other computing devices, using one or more networks. Such networks may include public networks such as the internet, private networks such as an institutional or personal intranet, or any combination of private and public networks. The networks may include any type of wired or wireless network, including but not limited to local area networks (LANs), wide area networks (WANs), wireless WANs (WWANs), wireless LANs (WLANs), mobile communications networks (e.g., 3G, 4G, Edge, etc.), and so forth. In some implementations, the communications between computing devices may be encrypted or otherwise secured. For example, communications may employ one or more public or private cryptographic keys, ciphers, digital certificates, or other credentials supported by a security protocol, such as any version of the Secure Sockets Layer (SSL) or the Transport Layer Security (TLS) protocol.

The system 600 may include any number of computing devices of any type. The computing device(s) may include, but are not limited to: a personal computer, a smartphone, a tablet computer, a wearable computer, an implanted computer, a mobile gaming device, an electronic book reader, an automotive computer, a desktop computer, a laptop computer, a notebook computer, a game console, a home entertainment device, a network computer, a server computer, a mainframe computer, a distributed computing device (e.g., a cloud computing device), a microcomputer, a system on a chip (SoC), a system in a package (SiP), and so forth. Although examples herein may describe computing device(s) as physical device(s), implementations are not so limited. In some examples, a computing device may include one or more of a virtual computing environment, a hypervisor, an emulation, or a virtual machine executing on one or more physical computing devices. In some examples, two or more computing devices may include a cluster, cloud, farm, or other grouping of multiple devices that coordinate operations to provide load balancing, failover support, parallel processing capabilities, shared storage resources, shared networking capabilities, or other aspects.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products, i.e., one or more modules of computer program instructions encoded on a computer readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "computing system" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) may be written in any appropriate form of programming language, including compiled or interpreted languages, and it may be deployed in any appropriate form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any appropriate kind of digital computer. Generally, a processor may receive instructions and data from a read only memory or a random access memory or both. Elements of a computer can include a processor for performing instructions and one or more memory devices for storing instructions and data. Generally, a computer may also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, implementations may be realized on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any appropriate form of sensory feedback, e.g., visual feedback, auditory feedback, or tactile feedback; and input from the user may be received in any appropriate form, including acoustic, speech, or tactile input.

Implementations may be realized in a computing system that includes a back end component, e.g., as a data server, or that includes a middleware component, e.g., an application server, or that includes a front end component, e.g., a client computer having a graphical UI or a web browser through which a user may interact with an implementation, or any appropriate combination of one or more such back end, middleware, or front end components. The components of the system may be interconnected by any appropriate form or medium of digital data communication, e.g., a communication network. Examples of communication networks include a local area network ("LAN") and a wide area network ("WAN"), e.g., the Internet.

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable sub-combination. Moreover, although features may be described above as acting in certain combinations and even initially claimed as such, one or more features from a claimed combination may in some examples be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claims.

What is claimed is:

1. A computer-implemented method performed by at least one processor, the method comprising:
   receiving, by the at least one processor, textual data that is typed into a chat client, by a first user during a time period, for communication to a second user, wherein the textual data comprises first natural language data;
   determining, by the at least one processor, a state of the first user during the time period when the textual data is typed into the chat client, the state determined based on biometric data that is generated by at least one sensor device measuring at least one physiological characteristic of the first user during the time period, wherein the at least one sensor device comprises a wearable device separate from the at least one processor;
   transforming, by the at least one processor, the textual data to generate transformed textual data and an emotional indicator based at least partly on the state, wherein the transformed textual data comprises second natural language data, the emotional indicator comprises an icon, a color, an image, a textual descriptor, an audio signal, or any combination thereof, corresponding to the state of the first user, and transforming the textual data to generate the transformed textual comprises:
      determining whether one or more dictionary entries correspond to the state of the first user;
      transforming the textual data into the transformed textual data using the one or more dictionary entries in response to the one or more dictionary entries corresponding to the state of the first user; and
      transforming the textual data into the transformed textual data using one or more default dictionary entries in response to the one or more dictionary entries not corresponding to the state of the first user, wherein the one or more default dictionary entries are emotion-agnostic; and
   communicating, by the at least one processor, the transformed textual data and the emotional indicator to be presented to the second user through an electronic display of a computing device.

2. The method of claim 1, wherein transforming the textual data includes translating the textual data from the first natural language data to generate the transformed textual data in the second natural language data.

3. The method of claim 2, wherein the translating includes:
   performing a first translation of at least a portion of the textual data from the first natural language data to generate at least a portion of the transformed textual data in the second natural language data;
   determining, based on an updated state of the first user, that the first translation is incorrect; and
   performing, based on the updated state of the first user, a second translation of at least the portion of the textual data from the first natural language data to generate at least the portion of the transformed textual data in the second natural language data.

4. The method of claim 3, comprising presenting the first translation for viewing by the first user during an additional time period.

5. The method of claim 4, comprising determining the updated state of the first user during the additional time period based on additional biometric data that is generated by the at least one sensor device measuring the at least one physiological characteristic of the first user during the additional time period.

6. The method of claim 1, wherein the transformed textual data is generated to include metadata that corresponds to the emotional indicator, the state of the first user, or both.

7. The method of claim 1, wherein the biometric data indicates a heart rate, a pulse, a perspiration level, a blood pressure, a galvanic skin response, a pupil dilation, a neural oscillation activity, or any combination thereof.

8. The method of claim 1, wherein transforming the textual data to generate the transformed textual data employs a convolutional neural network including at least one layer that performs an analysis based on the state of the first user.

9. The method of claim 1, wherein the emotional indicator comprises an emoticon, an emoji, or both.

10. The method of claim 9, wherein communicating the emotional indicator to be presented to the second user through a computing device comprises presenting the emoticon, the emoji, or both, in another chat client for viewing by the second user.

11. The method of claim 1, wherein the one or more dictionary entries correspond to a category of users including the first user, and the category of users comprises a demographic-based category, a location-based category, or both.

12. The method of claim 1, comprising determining, by the at least one processor, the state of the first user based on an increase or a decrease in typing speed of the first user over the time period.

13. A system, comprising:
   at least one processor; and
   a memory communicatively coupled to the at least one processor, the memory storing instructions which, when executed by the at least one processor, cause the at least one processor to perform operations comprising:
      receiving textual data that is typed into a chat client, by a first user during a time period, for communication to a second user, wherein the textual data comprises first natural language data;

determining a state of the first user during the time period when the textual data is typed into the chat client, the state determined based on biometric data that is generated by at least one sensor device measuring at least one physiological characteristic of the first user during the time period, wherein the at least one sensor device comprises a wearable device separate from the at least one processor;

transforming the textual data to generate transformed textual data and an emotional indicator based at least partly on the state, wherein the transformed textual data comprises second natural language data, the emotional indicator comprises an icon, a color, an image, a textual descriptor, an audio signal, or any combination thereof, corresponding to the state of the first user, and transforming the textual data to generate the transformed textual comprises:

determining whether one or more dictionary entries correspond to the state of the first user;

transforming the textual data into the transformed textual data using the one or more dictionary entries in response to the one or more dictionary entries corresponding to the state of the first user; and transforming the textual data into the transformed textual data using one or more default dictionary entries in response to the one or more dictionary entries not corresponding to the state of the first user, wherein the one or more default dictionary entries are emotion-agnostic; and communicating the transformed textual data and the emotional indicator to be presented to the second user through an electronic display of a computing device.

14. The system of claim 13, wherein transforming the textual data includes translating the textual data from the first natural language data to generate the transformed textual data in the second natural language data.

15. The system of claim 14, wherein the translating includes:

performing a first translation of at least a portion of the textual data from the first natural language data to generate at least a portion of the transformed textual data in the second natural language data;

determining, based on an updated state of the first user, that the first translation is incorrect; and performing, based on the updated state of the first user, a second translation of at least the portion of the textual data from the first natural language data to generate at least the portion of the transformed textual data in the second natural language data.

16. The system of claim 13, wherein the transformed textual data is generated to include metadata that corresponds to the emotional indicator, the state of the first user, or both.

17. The system of claim 13, wherein the emotional indicator comprises an emoticon, an emoji, or both.

18. One or more computer-readable media storing instructions which, when executed by at least one processor, cause the at least one processor to perform operations comprising:

receiving textual data that is typed into a chat client, by a first user during a time period, for communication to a second user, wherein the textual data comprises first natural language data;

determining a state of the first user during the time period when the textual data is typed into the chat client, the state determined based on biometric data that is generated by at least one sensor device measuring at least one physiological characteristic of the first user during the time period, wherein the at least one sensor device comprises a wearable device separate from the at least one processor;

transforming the textual data to generate transformed textual data and an emotional indicator based at least partly on the state, wherein the transformed textual data comprises second natural language data, the emotional indicator comprises an icon, a color, an image, a textual descriptor, an audio signal, or any combination thereof, corresponding to the state of the first user, and transforming the textual data to generate the transformed textual comprises:

determining whether one or more dictionary entries correspond to the state of the first user;

transforming the textual data into the transformed textual data using the one or more dictionary entries in response to the one or more dictionary entries corresponding to the state of the first user; and transforming the textual data into the transformed textual data using one or more default dictionary entries in response to the one or more dictionary entries not corresponding to the state of the first user, wherein the one or more default dictionary entries are emotion-agnostic; and communicating the transformed textual data and the emotional indicator to be presented to the second user through an electronic display of a computing device.

19. The one or more computer-readable media of claim 18, wherein the emotional indicator comprises an emoticon, an emoji, or both.

* * * * *